US006059751A

United States Patent [19]
Ostapchenko et al.

[11] Patent Number: 6,059,751
[45] Date of Patent: May 9, 2000

[54] DILATATION CATHETER BALLOONS WITH IMPROVED PUNCTURE RESISTANCE

[75] Inventors: George Joseph Ostapchenko, Wilmington, Del.; Donna Lynn Visioli, Lower Gwynedd, Pa.

[73] Assignee: E. I. du Pont de Nemours and Company, Wilmington, Del.

[21] Appl. No.: 09/245,794

[22] Filed: Feb. 5, 1999

Related U.S. Application Data

[62] Division of application No. 08/791,799, Jan. 29, 1997, Pat. No. 5,908,406
[60] Provisional application No. 60/006,514, Jan. 31, 1996.
[51] Int. Cl.[7] .......................... A61M 29/00; A61M 5/00; A61M 25/00
[52] U.S. Cl. .......................... 604/96; 604/280; 604/264; 604/915; 606/194; 428/35.7
[58] Field of Search ................................ 604/96, 280, 99, 604/264, 103, 915; 606/192, 194; 428/35.7

[56] References Cited

U.S. PATENT DOCUMENTS

| | | | |
|---|---|---|---|
| 4,490,421 | 12/1984 | Levy | 428/35 |
| 4,796,629 | 1/1989 | Grayzel | 123/344 |
| 5,195,969 | 3/1993 | Wang et al. | 604/96 |
| 5,270,086 | 12/1993 | Hamlin | 428/352 |
| 5,290,306 | 3/1994 | Trotta et al. | 606/194 |
| 5,304,134 | 4/1994 | Kraus et al. | 604/96 |
| 5,304,340 | 4/1994 | Downey | 264/521 |
| 5,328,468 | 7/1994 | Kaneko et al. | 604/96 |
| 5,447,497 | 9/1995 | Sogard et al. | 604/101 |

FOREIGN PATENT DOCUMENTS

| | | | |
|---|---|---|---|
| 2154516 | 1/1996 | Canada | C08G 81/00 |
| 0 566 755 | 10/1993 | European Pat. Off. | A61L 29/00 |
| 0 624 625 | 11/1994 | European Pat. Off. | C08L 67/02 |
| 0 531 117 | 1/1997 | European Pat. Off. | B29C 55/26 |
| 52-93490 | 8/1977 | Japan | B32B 27/32 |
| WO 91/17201 | 11/1991 | WIPO | C08J 5/02 |
| WO 92/19316 | 11/1992 | WIPO | A61M 29/00 |
| WO 94/04601 | 3/1994 | WIPO | C08J 7/00 |
| WO 95/09667 | 4/1995 | WIPO | A61M 29/00 |
| WO 95/23619 | 9/1995 | WIPO | A61L 29/00 |

OTHER PUBLICATIONS

P. M. Subramanian, Poly(Ethylene Terephthalate) Blends for Permeability Barrier Applications, *Polymer Engineering and Science*, 27(20), 1574–1581, Nov. 1987.
Encyclopedia of Polymer Science and Engineering, *Ionic Polymers*, 8, 393–423, 1988 ed.

*Primary Examiner*—James C. Housel
*Assistant Examiner*—S. Devi

[57] ABSTRACT

Multi-layer puncture-resistant biaxially oriented coextruded films or tubings are disclosed for use in dilatation balloon catheters. The catheter balloons so formed comprise a first, inner layer of an orientable thermoplastic resin; a second layer of a thermoplastic inomeric olefin copolymer secured to the outside surface of the first layer; and an optional third layer of an orientable thermoplastic resin secured to the outside surface of the second layer. Processes for forming the dilatation catheter balloons herein are also disclosed.

13 Claims, 1 Drawing Sheet

DILATATION CATHETER BALLOONS WITH IMPROVED PUNCTURE RESISTANCE

This application is a division of U.S. application Ser. No. 08/791,799 filed Jan. 29, 1997 U.S. Pat. No. 5,908,406 which claims the priority benefit of U.S. Provisional Application No. 60/006514 filed Jan. 31, 1996.

FIELD OF THE INVENTION

This invention relates to dilatation catheter balloons suitable for use in percutaneous transluminal coronary angioplasty. More particularly, this invention relates to such balloons exhibiting improved puncture resistance.

BACKGROUND OF THE INVENTION

Dilatation catheter balloons are used in invasive medical procedures such as percutaneous transluminal coronary angioplasty (PTCA). This particular procedure has become a tool of major importance in the treatment of coronary heart disease, as described by D. S. Baim, MD, in *Heart Disease, A Textbook of Cardiovascular Medicine,* 4th Edition, Chapter 41, E. Braunwald, Ed, published by W. B. Saunders Company, 1992. A vascular stenosis is relieved by expansion of a dilatation catheter balloon which has been introduced into the occluded blood vessel at the site of the lesion by way of a catheter.

U.S. Pat. No. 4,490,421 (Levy) discloses high strength, high modulus biaxially oriented articles exhibiting a preferred mode of failure, the process being particularly well-suited for the production of dilatation catheter balloons for invasive medical procedures, as taught therein.

It has been found in the practice of PTCA that a significant percentage of the stenoses relieved thereby are subject to restenosis, essentially a reversion to the previous occluded condition after removal of the balloon catheter. This may occur over a period of minutes, or may take weeks or months to occur. Increasingly, intraluminal prostheses known as stents are placed in the treated vessel to serve as a reinforcing member, and prevent the further accretion of materials at the location of the original lesion. Stents are for the most part made from metal wires or tubes. A preferred method for implantation of the stent is to place the stent around the outside of a balloon catheter. As the balloon is expanded to treat the lesion, the stent is simultaneously expanded. The balloon is subsequently deflated and withdrawn, leaving the stent in place.

During the dilatation procedure, the balloon is undesirably susceptible to puncture by the sharp edges of the stent during the expansion and implantation phase of treatment. A puncture so caused then induces a failure in the balloon, forcing the procedure to be aborted, thus subjecting the patient to unnecessary risk and adding undesirably to the cost of the procedure It is known that improved puncture resistance of dilatation catheter balloons may be achieved by forming them from a coextruded tubular article wherein the inner layer is a polymer suitable for use as a dilatation catheter balloon, e.g., polyethylene terephthalate (PET), and a second layer is a more rubbery or so-called "toughened" composition affording improvements in puncture resistance. The tougher or more rubbery layer is resident on the outside of the catheter balloon, adjacent to the inside surface of the stent. For example, U.S. Pat. No. 5,290,306 discloses the use of a thermoplastic elastomer, of a hardness less than 55 D according to ASTM D2240, preferably a polyurethane, as the outer layer in a biaxially oriented coextruded tubular article wherein the inner layer is PET or polyamide. U.S. Pat. No. 5,195,969 discloses a biaxially oriented coextruded tubular article consisting of an inner layer of PET film and an outer layer of a so-called toughened blend of PET. These articles are said to exhibit improved puncture resistance.

It is thus highly desirable to provide a puncture-resistant dilatation catheter balloon suitable for use in PTCA accompanied by the implantation of vascular stents, and in other medical dilatation procedures.

SUMMARY OF THE INVENTION

The present invention provides for a dilatation catheter balloon suitable for use in PTCA, comprising a first, inner layer comprising at least 80% by weight of a biaxially oriented thermoplastic resin selected from the group consisting of polyesters, polyamides, polyolefins, and blends thereof, and up to 20% by weight of a thermoplastic elastomer selected from the group consisting of polyurethanes, polyether-ester block copolymers, and modified olefin copolymers, the first, inner layer having an inside surface and an outside surface and a thickness of 5–56 micrometers. A second layer of a thermoplastic ionomeric olefin copolymer; also having an inside surface and an outside surface and a thickness of 0.5–5 micrometers, is provided with the inside surface thereof secured to the outside surface of the first, inner layer.

Another embodiment of the present invention provides for a third layer comprising at least 80% by weight of a biaxially oriented thermoplastic resin selected from the group consisting of polyesters, polyamides, polyolefins, and blends thereof, and up to 20% by weight of a thermoplastic elastomer selected from the group consisting of polyurethanes, polyether-ester block copolymers, and modified olefin copolymers. This layer has an inside surface and an outside surface and a thickness of 1–5 micrometers; the inside surface thereof is secured to the outside surface of the second layer. Optionally other layers as disclosed herein may be applied as desired concurrently with or subsequent to the fabrication of the multi-layer catheter balloon of this invention.

The present invention further provides for a dilatation catheter balloon suitable for use in PTCA, comprising a melt blend of at least 80% of a biaxially oriented thermoplastic resin polymer as disclosed hereinabove and up to 20% by weight of a thermoplastic elastomer also as disclosed hereinabove. The resulting catheter balloon has a single wall thickness of 7–75 micrometers.

Regarding materials selection, in a preferred embodiment the biaxially oriented thermoplastic resin is polyethylene terephthalate. The thermoplastic elastomer is desirably a polyetherester block copolymer.

The dilatation catheter balloons described herein may be prepared according to the process of the present invention. The process comprises forming a tube comprising a first inner layer, a second layer, and optionally a third layer. Each layer has both inside and outside surfaces; the layers are arranged such that the inside surface of the second layer is secured to the outside surface of the first inner layer, and the inside surface of the third layer is secured to the outside surface of the second layer. The first inner layer comprises at least 80% by weight of a biaxially orientable thermoplastic resin as disclosed hereinabove and up to 20% by weight of a thermoplastic elastomer as disclosed hereinabove. It has a thickness of 5–56 micrometers. The second layer is a thermoplastic ionomeric olefin copolymer having a thickness of 0.5–5 micrometers. The optional third layer is selected from the materials of the first inner layer. The layers are fused concurrently or consecutively with formation of the tube. The tube is quenched and biaxially oriented to produce a dilatation catheter balloon. The catheter balloon is heat set.

Dilatation catheter balloons may also be prepared according to this process using the melt blends described herein. In such cases, the fusion step is necessarily obviated.

DETAILED DESCRIPTION OF THE INVENTION

Figure 1A:
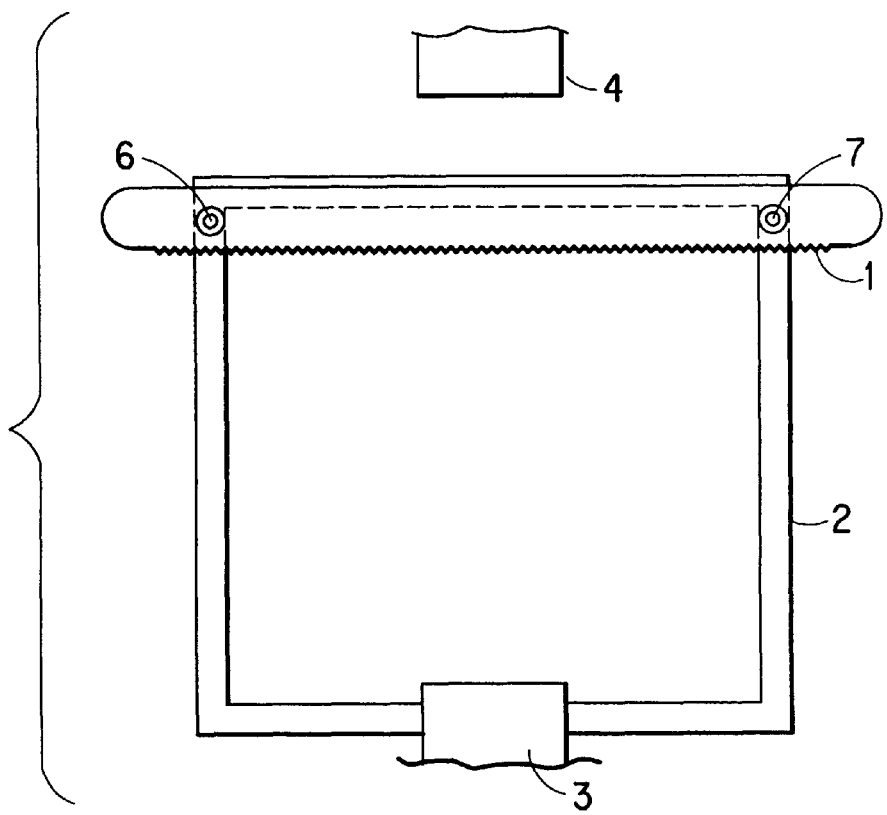
FIG. 1A is a side view of the apparatus used for determining puncture resistance according to the invention.
Figure 1B:
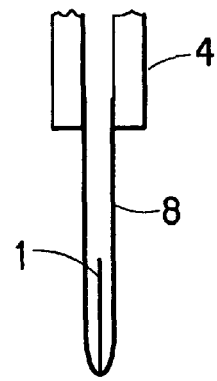
FIG. 1B is a view of a portion of the apparatus of FIG. 1A including the film sample to be tested.

The fabrication of dilatation catheter balloons from extruded polymeric tubing is well known in the art, and is described in Levy (U.S. Pat. No. 4,490,421) which is incorporated by reference herein. The process for fabrication of dilatation catheter balloons therein described is preferred for the practice of the present invention. However, in the present invention, a coextrusion process is employed to produce the multi-layer construction of the present invention. Coextrusion is well-known in the art, as described for example beginning on page 608 of the Encyclopedia of Polymer Science, second edition, vol. 6, John Wiley & Sons, New York (1985).

Thermoplastic ionomeric olefin copolymers offer several improvements over the known art. In comparison to thermoplastic elastomers (TPE's), most specifically the polyurethane of the art, ionomers are less costly, crystallize more quickly permitting quicker molding cycle times, and are less subject to thermal degradation when briefly exposed to high temperatures. In comparison to toughened PET blends, ionomers are less costly and tougher. Additionally, ionomers are also known as excellent heat sealing agents, and thus incorporation of the ionomer into, e.g., a catheter balloon affords improved structural integrity of the assembly without resort to adhesives.

In one embodiment of the present invention, PET and an ionomeric olefin copolymer are combined in a biaxially oriented two-layer catheter balloon wherein the outer layer is the ionomeric olefin copolymer. The PET is preferably of an intrinsic viscosity in the range of 0.5–1.1, most preferably in the range of 0.8–1.1. The thermoplastic ionomeric olefin copolymer is preferably of a melt index (MI) of less than 5 according to ASTM D-1238, a flexural modulus of less than about 250 MPa according to ASTM D-790, most preferably about 100 MPa In life-critical medical procedures such as PTCA, it is desirable to prevent the balloon from bursting while it is inflated. Bursting can be caused either by a tensile failure of the balloon under the stress of the pressure of the inflating fluid, or by puncture, as hereinabove discussed. Tensile strength of the balloon can be maximized for given materials of construction by increasing the thickness of the strength member. That is, the inner layer must be as thick as possible. Similarly, the toughening or puncture-resistant layer, which is the ionomeric olefin copolymer layer, must be sufficiently thick to provide sufficient protection against puncture.

In the practice of PTCA and related procedures it is found that there are practical limits to the overall thickness of the balloons which are employed therein. In the two-layer embodiment of the present invention, the thickness of the first, inner layer is 5–56 micrometers, preferably 9–27 micrometers, most preferably 1 1–19 micrometers. The thickness of the second, outer ionomer layer is 0.5–5 micrometers, preferably 0.6–2 micrometers, most preferably 0.8–1 micrometers.

In use, the two layer oriented article of the present invention is disposed whereby the ionomer layer is presented to the potential source of puncture. Thus in the two-layer dilatation catheter balloon of this invention, the ionomer layer resides on the outside of the balloon, and is the first upon which, as the balloon is inflated, is impinged the stent.

It is found in the practice of the present invention that when the outer ionomer layer directly contacts the wall of the mold during orientation of the two layer balloon as described in U.S. Pat. No. 4,490,421, it is difficult to remove because of the high adhesion properties ot the ionomer. Numerous methods are available for securing release of the two-layer oriented balloon from the mold. Among these are cooling the mold from the orientation temperature to a temperature in the range of −18° to 10° C. by circulating chilled water or refrigerant through the mold using known methods. Use of a release-coated mold, such as a mold coated with a fluoropolymer film, is also known to afford good release properties. Finally, use of a so-called "mold release" spray prior to orientation molding is also an effective means for obtaining release. The cooling method is preferred because it eliminates the chance of surface contamination of the catheter balloon. However, the cooling method involves a severe penalty in cycle time, and therefore productivity.

In another embodiment of this invention, a third polymeric film layer, selected from the same group as the first layer, is coextruded with the first two, such that the second, ionomeric layer is sandwiched between the two, the third layer being contiguous with and outwardly disposed upon the ionomeric layer. The third layer is preferably 1–5 micrometers in thickness, most preferably 2–4 micrometers. It is found in the practice of this invention that the thin third layer, preferably of PET, provides excellent mold-release with no need to resort to any additional measures to secure that release.

It is a particularly surprising aspect of the present invention that the three-layered oriented catheter balloons of this invention provide significant improvements in puncture resistance with respect to otherwise comparable two-layered catheter balloons. In laboratory testing, as hereinbelow described, when the thin third layer of a three layer film was presented to the puncture source, the puncture resistance was improved by 50–200% over that obtained from the two layer film, and over that obtained by presenting the first, or thicker, layer of the three layer film, to the puncture source.

It should be noted that films were tested because of their relative ease of preparation. Because all such films tested were biaxially oriented, one skilled in the art would expect the same results with dilatation catheter balloons made from these films.

In a preferred embodiment of the process of this invention, each resin or resin blend to be used is charged in the form of pellets or powder, preferably pellets, to a separate extruder wherein it is melted and fed in the melt to a multi-layer combining feed block adaptor whence it is fed to a tubular die, wherein the layers are formed and extruded. The thickness ratio of the layers is determined by the respective flow rates of the different melt streams, these being determined primarily by adjusting the extruder screw speeds as appropriate for obtaining the desired result. While the dictates of economy and convenience point towards using the fewest extruders to produce a layered article with the smallest numbers of layers which will meet the particular objectives of the application, there is no limitation in principle on the number of extruders which may be employed, the number of resins which may be employed, or the number of layers in the resultant coextruded article.

Differences in melting points and degradation rates must be taken into account when coextruding dissimilar polymers. For example, in a preferred embodiment of the present invention, PET resin of an intrinsic viscosity in the range of 0.55 to 1.1 is coextruded with a thermoplastic ionomeric olefin copolymer preferred for the practice of this invention. The PET extruder is preferably operated at ca. 275° C., while the olefin ionomer extruder is operated at ca. 200° C. The molten outputs of the extruders are fed to a combining feed block in which the two melts are combined just prior to passing through the extrusion die. In order to keep the PET molten, the block and die must be kept at ca. 265° C. However, at that temperature, the ionomer will begin to degrade, primarily by cross-linking, creating a potential for plugging up the coextrusion assembly with degraded material and degrading the performance of the composite so-produced. In order to minimize the potential for a problem, the residence time of the ionomer in the block and die must be kept to less than 10 minutes, preferably less than 5 minutes. Residence time can be adjusted by adjusting extruder screw speeds, die gaps, and take-off rates.

In another preferred embodiment of the process of this invention a two or three layer film is coextruded into tube which is quenched by immersing the tubing in a water bath maintained at ca. 40° C., followed by orientation as described in Levy.

In another embodiment of the present invention, a melt blend of PET and a thermoplastic elastomer, preferably a block copolyetherester, is fabricated into a single-layer tubing which is subject to orientation and fabrication into a dilatation catheter balloon in the manner described for unblended PET in Levy. The resultant film or catheter balloon exhibits improved puncture resistance with little loss of burst strength. The composition of this embodiment may also be substituted for the unblended PET in the multi-layer embodiments hereinabove described.

Although the art teaches that blends of PET and block copolyetherester thermoplastic elastomers preferably contain at least 40% of the TPE, it is a particularly surprising aspect of the present invention that puncture resistance is improved by 50% or greater by the addition of less than 20% TPE to PET, while tensile strength is reduced only slightly. The catheter balloons formed from the melt blends of the present invention retain more PET than the balloons of the art, and thus desirably exhibit higher burst strengths. The melt blend of the present invention comprises 80–100%. preferably 85–95% of PET subject to the limitations hereinabove described and 0–20%, preferably 5–15%, of a thermoplastic elastomer, preferably a copolyether ester block copolymer, most preferably a copolyetherester block copolymer having a Melt Flow Rate of less than 15 (ASTM D-1238) and a hardness of >50 D according to ASTM D-2240 (Shore hardness).

The melt blend of this embodiment is achieved by any conventional means known in the art. Good practice in the art teaches that the requisite amounts of each resin be first melt blended, preferably in a twin screw extruder designed for that specific task, and blend pellets fabricated therefrom the pellets being subsequently extruded, preferably in a single-screw extruder designed for the purpose, into tubing. Orientation may be performed in the same manner as for the other embodiments of this invention.

EXAMPLES

Procedures

The improvements offered by this invention are further described in the following specific embodiments. In the examples below, flat films were extruded as described in each example, and melt cast onto a rotating quench roll at 60° C. Samples 105×105 mm were prepared from the continuous cast film, and biaxially oriented as indicated using a pantograph stretcher manufactured by T. M. Long Co., Somerville, N.J., at 92° C., followed by air quenching. The films so oriented were then heat set by clamping the films under tension between frames with a 254 mm square inner edge and heating at 180° C. for one minute in a Blue M oven, model CFD1OF-4, available from Blue M Electric, Blue Island, Fla.

Having reference to FIG. 1A and B, the apparatus shown therein was employed for determining puncture resistance according to the following procedure. A fine tooth saw blade 1 ("Greenstripe" type SF1218 manufactured by L. S. Starrett Co., Athol, Mass.) was mounted on the top member of a stainless steel frame 2 3.18 mm in thickness, with inner dimensions of 127×127 mm, by fasteners 6 and 7 so that the saw teeth extended 3.8 mm beyond the inside edge of the frame 2. The bottom member of the frame 2 was clamped by lower clamp 3 in the lower jaw (not shown) of a Tensile Testing Machine model 2W manufactured by Systems Integration Technology, Inc., Staughton, Mass. The position of the upper jaw (not shown) of the machine was adjusted so that the edge of the saw blade 1 was 38 mm below the jaw. A film specimen 8 of dimensions 127 mm long and 25.4 mm wide was looped through the frame 2 and the two ends of the film specimen 8 secured in the upper clamp 4 of the testing machine so that the middle of the film specimen 8 was in contact with the teeth of the saw blade 1. The jaws were then separated at a rate of 50.8 mm/sec and the applied force and time to failure were determined, and the energy to break was determined therefrom.

Energy to break was then divided by the thickness of the test specimen to normalize for specimen thickness. This test was both a more realistic and more severe test than the standard test. Instead of a single probe of 1.52 mm radius as in ASTM F 1306-90, the test employed in the examples herein described involved multiple contact points with radii of 0.028 mm. A stent employed with a dilatation catheter balloon to prevent restenosis will contact the outside surface of the balloon at multiple points.

Instrinsic Viscosity (IV) was determined using the method of ASTM D5225-92 except that the solvent employed was a 50/50 mixture of trichloroacetic acid and methylene chloride.

Comparative Example 1

A linear high molecular weight PET homopolymer sold under the trademark SELAR PT X280, available from E. I. du Pont de Nemours and Company, and having an IV of 1.1 was extruded using a 25.4 mm single screw extruder, available from Killion, Inc., Vernon, N.J., and a 15.2 cm wide coat hanger film die with the die opening set at 0.51 mm. Films were extruded at 116 cm/min at a screw speed of 40 rpm and extruder temperature at 280° C. The extruded film was ca. 0.24 mm thick. Nine film specimens were oriented biaxially 250% in each direction, and heat set. The resulting films ranged in thickness from 0.016 mm to 0.022 mm and exhibited an average normalized energy to break of 0.12±0.02 in-lb/mil.

Examples 1–3 and Comparative Example 2

Two layer biaxially oriented films were prepared by simultaneous extrusion of SELAR PT X280 and the resins listed in Table 1. SURLYN is the trademark of an ionomeric resin made from a copolymer of ethylene and methacrylic acid, neutralized with either zinc or sodium to form the ionomer and available from E. I. du Pont de Nemours and Company. SURLYN 9020 is a zinc ionomer with a Melt Index (ASTM D-1238) of 1.1. SURLYN 9721 is a zinc monomer with a Melt Index of 1.0. SURLYN 8020 is a sodium ionomer with a Melt Index of 1.0. HYTREL 4056 is the trademark for a low modulus, extrusion grade block copolyetherester thermoplastic elastomer characterized by a Shore hardness of 40 D (ASTM D-2240), and available from E. I. du Pont de Nemours and Company. The SELAR PT X280 was extruded through a 3.81 cm single screw extruder, available from Killion, Inc., Vernon, N.J., at 32 rpm and ca. 275° C. The SURLYN and HYTREL 4056 resins of Table I were extruded through a 3.18 single screw Killion extruder operating at 5 rpm and a temperature of 200° C. the molten output of the two extruders was directed through a two-layer combining feed block, adaptor with a 35.6 cm wide slot die having a 0.38 mm die gap. The feed block and die were maintained at ca. 265° C. The samples so produced were quenched, oriented and heat set as hereinabove specified, and are described in Table 1. In all cases, the PET layer of the bilayer film was in contact with the 60° C. quench drum.

In order to accurately determine the respective thicknesses of the film layers, the layers were delaminated by affixing a piece of pressure sensitive adhesive tape to the two sides of the film and then pulling them apart. The SELAR PT X280/HYTREL laminates could not be separated in that manner.

The film of Comparative Example 2, was a film of the art of Trotta et al. (U.S. Pat. No. 5,290,306). Table 2 lists the results obtained from the puncture test hereinabove described. In each case, layer 2 was in initial contact with the saw blade. Each datum represents an average of three determinations.

TABLE 1

Description of Two-Layer Films

| | Layer 1 | | Layer 2 | |
|---|---|---|---|---|
| | Resin | Thickness (μm) | Resin | Thickness (μm) |
| Example 1 | SELAR PT X280 | 24.1 | SURLYN 9020 | 1.3 |
| Example 2 | SELAR PT X280 | 26.7 | SURLYN 9721 | 1.3 |
| Example 3 | SELAR PT X280 | 29.2 | SURLYN 8020 | 2.5 |
| Comp. Ex. 2 | SELAR PT X280 | NA | HYTREL 4056 | NA |

TABLE 2

Puncture Resistance Results on Two-Layer Films

| | Energy to Break, in-lb/mil | % Change vs. Comp. Ex. 1 |
|---|---|---|
| Example 1 | 0.18 | +50 |
| Example 2 | 0.34 | +190 |
| Example 3 | 0.22 | +90 |
| Comp. Ex. 5 | 0.27 | +130 |

Examples 4–10

Three-layer biaxial films, described in Table 3, were prepared by simultaneously extruding two layers of SELAR PT X280 on either side of a layer of the resins indicated in Table 3. The SELAR PT X280 was extruded as in Examples 1–3 except that the screw speed was 38 rpm. The middle layer resins were extruded through the 2.54 cm single screw extruder of Comparative Example 1, operated in the range of 6–14 rpm, and at a temperature of ca. 220° C. The extruder outputs were fed to a three-layer combining feed block adapter and a 35.6 cm wide slot die having a 0.38 mm die gap to obtain a film of ca. 0.24 mm thickness. The films were quenched, oriented and heat set as hereinabove described. In all cases, layer 3 was in contact with the 60° C. quench drum. Film layer thickness was determined as described for Examples 1–3.

TABLE 3

Description of Three-Layered Films

| | Layer 1 | | Layer 2 | | Layer 3 | |
|---|---|---|---|---|---|---|
| Example | Resin | Thickness (μm) | Resin | Thickness (μm) | Resin | Thickness (μm) |
| 4 | SELAR PT X280 | 2.5 | SURLYN 9721 | 2.5 | SELAR PT X280 | 15 |
| 5 | SELAR PT X280 | 2.5 | SURLYN 9721 | 1.1 | SELAR PT X280 | 15 |
| 6 | SELAR PT X280 | 2.5 | SURLYN 9721 | 0.8 | SELAR PT X280 | 17 |
| 7 | SELAR PT X280 | 3.8 | SURLYN 8020 | 1.0 | SELAR PT X280 | 14 |
| 8 | SELAR PT X280 | 2.5 | SURLYN 9020 | 1.3 | SELAR PT X280 | 14 |
| 9 | SELAR PT X280 | 2.5 | SURLYN 9020 | 1.1 | SELAR PT X280 | 15 |
| 10 | SELAR PT X280 | 2.5 | SURLYN 9020 | 1.1 | SELAR PT X280 | 15 |

The puncture resistance results are shown in Table 4. All of these results were obtained with the thick layer, layer 3, in contact with the saw blade. Each datum is an average of three determinations.

TABLE 4

Puncture Resistance Results on Three-layer Films - Layer 3 Towards Blade

| | Normalized Energy To Break (in-lb/mil) | % Change vs. Comp. Ex. 1 |
|---|---|---|
| Example 4 | 0.21 | 75 |
| Example 5 | 0.20 | 67 |
| Example 6 | 0.22 | 83 |
| Example 7 | 0.21 | 75 |
| Example 8 | 0.21 | 75 |
| Example 9 | 0.22 | 83 |
| Example 10 | 0.19 | 59 |

Examples 11–13

Additional specimens of oriented, heat set film of the extruded film of Example 8 were prepared as hereinabove described. They were oriented biaxially 225% in each direction. The films are described in Table 5. Rupture resistance was determined for Example 11 with Layer 3 in contact with the saw blade, as in Example 8. Those for Examples 12 and 13 with Layer 1 in contact with the saw blade. Results are shown in Table 6.

TABLE 5

Description of Three Layer Films

| | Layer 1 | | Layer 2 | | Layer 3 | |
|---|---|---|---|---|---|---|
| Example | Resin | Thickness (μm) | Resin | Thickness (μm) | Resin | Thickness (μm) |
| 11 | SELAR PTX 280 | 2.5 | SURLYN 9020 | 1.3 | SELAR PT X280 | 14 |
| 12 | SELAR PTX 280 | 2.5 | SURLYN 9020 | 1.3 | SELAR PT X280 | 14 |
| 13 | SELAR PTX 280 | 2.5 | SURLYN 9020 | 1.3 | SELAR PT X280 | 14 |

TABLE 6

Puncture Resistance of Films

| | Layer in Contact with Saw Blade | Normalized Energy to Break (in-lb/mil) | % Change relative to Comp. Ex. 1 |
|---|---|---|---|
| Example 11 | Layer 3 (Thick) | 0.21 | 75 |
| Example 12 | Layer 1 (Thin) | 0.49 | 400 |
| Example 13 | Layer 1 (Thin) | 0.89 | 640 |

Example 14 and Comparative Example 3

In Comparative Example 3, SELAR PT X280 was extruded into a single layer film using a 28 mm co-rotating, twin screw extruder manufactured by Werner and Pfleiderer, Inc., Ramsey, N.J. Screw speed was 100 rpm. Temperatures, quenching and orientation were as stated hereinabove. As Example 14, a melt blend of 85% by weight SELAR PT X280 and 15% by weight HYTREL 8238, the trademark for a high modulus mold extrusion grade (Shore hardness=82D, ASTM D-2240) copolyetherester thermoplastic elastomer and available from E. I. du Pont de Nemours and Company was extruded in a single-layer film under the same conditions as those for Comparative Example 3. Both were oriented as hereinabove described, biaxially 250% in each direction. The SELAR PT X280 film had a thickness of 17 micrometers and the blend film had a thickness of 16 micrometers.

The film of Comparative Example 3 exhibited a normalized energy to break of 0.16 in-lb/mil (33% higher than that of Comparative Example 1), while the film of Example 14 exhibited a normalized energy to break of 0.24 in-lb/rail, or an improvement of 50% over that of Comparative Example 3.

Examples 15–17 and Comparative Example 4

Three-layer biaxially oriented heat set films were prepared by coextruding, orienting and heat setting a blend comprising 85% SELAR PT X280 and 15% HYTREL 8238 with SURLYN 9020 and HYTREL 4056 in the manner described in Examples 4–10. The films are described in Table 7. In each case, Layer 3 (the thick layer) was presented to the saw blade. Table 8 shows the results.

TABLE 7

3-Layer Films of PET/HYTREL Blend

| | Layer 1 | | Layer 2 | | Layer 3 | |
|---|---|---|---|---|---|---|
| Example | Resin | Thickness (μm) | Resin | Thickness (μm) | Resin | Thickness (μm) |
| 15 | SELAR PT X280/ HYTREL 8238 | 2.5 | SURLYN 9020 | 1.3 | SELAR PTX 280/ HYTREL 8238 | 16 |
| 16 | SELAR PT X280/ HYTREL 8238 | 2.54 | SURLYN 9020 | 1.5 | SELAR PT X280/ HYTREL 8238 | 14 |
| 17 | SELAR PT X280/ HYTREL 8238 | 2.54 | SURLYN 9020 | 1.3 | SELAR PT X280/ HYTREL 8238 | 14 |
| Comp 4 | SELAR PT X280/ HYTREL 8238 | NA | HYTREL 4056 | NA | SELAR PT X280/ HYTREL 8238 | NA |

TABLE 8

Puncture Resistance of Films

| | Normalized Energy to Break (in-lb/mil) | % Change relative to Comp. Ex. 1 |
|---|---|---|
| Example 15 | 0.22 | 83 |
| Example 16 | 0.3 | 150 |
| Example 17 | 0.27 | 125 |
| Comparative Example 4 | 0.26 | 117 |

Comparative Example 5

Two layer tubing was made by simultaneously extruding a high molecular weight, linear PET homopolymer sold under the trademark SELAR PT 7451, available from E. I. du Pont de Nemours and Company and having an IV of 0.95 as an inner layer and SURLYN 8020 as an outer layer through a Canterbury Engineering Co. tri-layer tubing die by idling one of the layer positions. The SELAR PT 7451 was extruded with a 2.54 cm single-screw Killion extruder maintained at 275° C. and a screw speed of 12 rpm. The SURLYN 8020 was extruded with a 1.91 cm extruder, manufactured by Genca, Clearwater, Fla., maintained at 210° C. and a screw speed of 17 rpm. The tri-layered die was maintained at 280° C. The 0.8 mm (outside diameter), 0.36 mm inside diameter tube was produced at a rate of 32.6 m/min. the polymer flow rates through the die were adjusted by valves to obtain a SELAR PT 7451 layer thickness of 0.14 mm and a SURLYN 8020 ionomer layer thickness of 0.04 mm. Attempts to form 3.0 mm outside diameter angioplasty balloons using the method described in U.S. Pat. No. Re. 32,983 resulted in formed balloons that could not be removed from the mold without damage to the balloon because of ionomer layer adhesion to the outer wall of the balloon mold.

Examples 18 and 19

The film of Examples 11–13 was prepared into two specimens. In the first, that of Example 18, the thick layer of SELAR PT X280 (layer 3) was stripped off the remaining two layers, thus exposing a layer of SURLYN 9020. In Example 19, the 3 layer film was left intact. The specimens thus prepared were individually placed between sheets of aluminum foil, the assembly resulting therefrom being placed between the heated platens of a model 2699 Carver Laboratory Press, manufactured by Fred S. Carver, In, Menomonee Falls, Wis., and subject to 500 psi ram pressure and temperature for 1 minute, as described in Table 9. After pressing, an effort was made to remove the specimens from the aluminum sheets. Observations are given in Table 9.

TABLE 9

| | 60° C. | 90° C. | 280° C. |
|---|---|---|---|
| Example 18 | SELAR PT 7451 released without effort. SURLYN layer released but was tacky | SELAR PT 7451 layer released without effort. SURLYN layer released but with considerable effort | SELAR PT 7451 layer released with effort. SURLYN layer was completely adhered to foil. |
| Example 19 | Both sides released without effort | Both sides released without effort | Film did not completely release |

Comparative Example 6

Attempts to produce two-layer tubing using the method of Comparative Example 5 using a melt extrudable polyurethane, the preferred embodiment of the art of U.S. Pat. No. 5,290,306 (Trotta et al), in place of the SURLYN 9721 ionomer, were not successful because the polyurethane degraded in the die.

We claim:

1. A process for forming a dilatation catheter balloon suitable for use in percutaneous transluminal coronary angioplasty comprising:

forming a tube comprising a first, inner layer comprising at least 80% by weight of a biaxially orientable thermoplastic resin selected from the group consisting of polyamides, polyesters, polyolefins, and blends thereof, and up to 20% by weight of a thermoplastic elastomer selected from the group consisting of polyurethanes, poly-ether ester block copolymers, and modified olefin copolymers, said first layer having an inside surface and an outside surface and a thickness of 5–56 micrometers; a second layer of a thermoplastic ionomeric olefin copolymer, said second layer having an inside surface and an outside surface and a thickness of 0.5–5 micrometers, with the inside surface thereof secured to the outside surface of said first, inner layer; and optionally a third layer comprising at least 80% by weight of a biaxially oriented thermoplastic resin selected from the group consisting of polyamides, polyesters, polyolefins, and blends thereof, and up to 20% by weight of a thermoplastic elastomer selected from the group consisting of polyurethanes, poly-ether ester block copolymers, and modified olefin copolymers, said third layer having an inside surface and an outside surface and a thickness of 1–5 micrometers, with the inside surface thereof secured to the outside surface of said second layer;

fusing said layers concurrently or consecutively therewith;

quenching the tube so formed;

biaxially orienting the tube to produce a catheter balloon; and heat setting the biaxially oriented catheter balloon.

2. A process for forming a dilatation catheter balloon suitable for use in percutaneous transluminal coronary angioplasty comprising, forming a tube from a melt blend having 80–95% by weight of an orientable thermoplastic resin selected from the group consisting of polyamides, polyesters, polyolefins, and blends thereof, and 5–20% by weight of a thermoplastic elastomer having a hardness of about 82 D, or more, and selected from the group consisting of polyurethanes, polyether-ester block copolymers, and modified olefin copolymers;

quenching the tube so formed;

biaxially orienting the tube to produce a catheter balloon; and heat setting the biaxially oriented catheter balloon.

3. The process of claim 2 wherein the thermoplastic elastomer has a hardness of 82D.

4. The process of claim 3 wherein the thermoplastic elastomer is a copolyetherester thermoplastic elastomer.

5. The process of claim 2 wherein the orientable thermoplastic is polyethylene terephthalate.

6. The process of claim 1 wherein the thickness of said first, inner layer is from 9 to 27 micrometers, and the thickness of said second layer is 0.6–2 micrometers.

7. The process of claim 6 wherein the thickness of said third layer is from 2 to 4 micrometers.

8. The process of claim 1 wherein the biaxially oriented thermoplastic resin is polyethylene terephthalate.

9. The process of claim 8 wherein the polyethylene terephthalate has an intrinsic viscosity of from 0.5 to 1.1.

10. The process of claim 1 wherein the thermoplastic elastomer is a polyetherester block copolymer.

11. The process of claim 1 wherein the thermoplastic ionomeric olefin copolymer has a melt index of less than 5 and a flexural modulus of less than 250 MPa.

12. The process of claim 2 wherein the biaxially oriented thermoplastic resin is polyethylene terephthalate and the thermoplastic elastomer is a polyetherester block copolymer.

13. The process of claim 12 wherein the polyethylene terephthalate has an intrinsic viscosity of from 0.5 to 1.1.

* * * * *